United States Patent [19]

Friedman et al.

[11] 3,996,270

[45] Dec. 7, 1976

[54] INTERMEDIATE FOR GOSSYPLURE, THE SEX PHEROMONE OF THE PINK BOLLWORM

[75] Inventors: Lester Friedman, Cleveland; Henry H. Chanan, Cleveland Heights, both of Ohio

[73] Assignee: Story Chemical Corporation, Muskegon, Mich.

[22] Filed: June 24, 1974

[21] Appl. No.: 482,760

[52] U.S. Cl. .................. 260/488 H; 260/345.9; 260/491; 260/496; 260/632 Y; 260/642 C; 260/678; 424/84
[51] Int. Cl.[2] ............................... C07C 69/145
[58] Field of Search .......... 260/488 H, 491, 632 Y

[56] References Cited
OTHER PUBLICATIONS

P. E. Sonnet, J. Org. Chem., V. 39, No. 25, Dec. 1974, pp. 3793–3794.
Chem. Abstracts, 77: 100662a.

*Primary Examiner*—Vivian Garner
*Attorney, Agent, or Firm*—Cooper, Dunham, Clark Griffin & Moran

[57] ABSTRACT

The sex pheromone of the pink bollworm (*Pectinophora gossypiella*) is an approximate 1:1 mixture of (Z,Z)- and (Z,E)-7,11-hexadecadienyl acetate; this sex pheromone, the above-identified mixture of isomers, is known as Gossyplure. A component of Gossyplure, (Z,E)-7,11-hexadecadienyl acetate, is the sex pheromone of the Angoumois grain moth (*Sitotroga cerealella*) and is known as Angoulure. An isomeric component of Gossyplure, the Z,Z isomer, elicits no response from the male Angoumois grain moth and it appears that the relatively large amount of the Z,Z isomer in Gossyplure interferes with the Z,E isomer such that Gossyplure cannot be used as a substitute for Angoulure. The isomeric components of Gossyplure are manufactured by the butylation of the mono-anion of 1,5-hexadiyne to 1,5-decadiyne which is in turn alkylated with hexamethylene halohydrin or a protective derivative thereof, such as tetrahydropyranyl ether, to give the 7,11-hexadecadiynyl moiety which after acetylation and partial reduction affords (Z,Z)-7,11-hexadecadienyl acetate, one of the isomeric components of Gossyplure. The other isomeric component of Gossyplure, the Z,E isomer, which is also known as Angoulure, the sex pheromone of the Angoumois grain moth, is synthesized from deca-(E)-5-enyne, (prepared by sodium-liquid ammonia reduction of 1,5-decadiyne) in an analogous manner.

1 Claim, No Drawings

INTERMEDIATE FOR GOSSYPLURE, THE SEX PHEROMONE OF THE PINK BOLLWORM

This invention relates to insect sex pheromones, methods of their manufacture and compounds useful in the manufacture of insect sex pheromones.

The sex pheromone of the pink bollworm, *Pectinophora gossypiella*, is an approximate 1:1 mixture of (Z,Z)- and (Z,E)-7,11-hexadecadienyl acetate. This sex pheromone, the above-identified mixture of isomers, is known as Gossyplure. A component of Gossyplure, (Z,E)-7,11-hexadecadienyl acetate, is the sex pheromone of the Angoumois grain moth, Sitotroga cerealella, and is known as Angoulure. An isomeric component of Gossyplure, the Z,Z isomer, elicits no response from the male Angoumois grain moth and it appears that the relatively large amount of the Z,Z isomer in Gossyplure interferes with the Z,E isomer such that Gossyplure cannot be used as a substitute for Angoulure.

The isomeric components making up Gossyplure, i.e. (Z,Z)- and (Z,E)-7,11-hexadecadienyl acetate, are important materials. For example, the Z,E component, known as Angoulure, is useful for the control of the Angoumois grain moth and the 1:1 mixture of the Z,Z and Z,E isomers, known as Gossyplure, is useful in monitoring and/or controlling the pink bollworm, a serious economic pest of western cotton. The isolation or recovery of Gossyplure from natural sources, i.e. the female bollworm, is essentially not economic because of the extremely low levels present in each adult female pink bollworm.

It is an object of this invention to provide a method for the manufacture of Gossyplure, the sex pheromone of the female pink bollworm.

It is another object of this invention to provide a method for the manufacture of Angoulure, the sex pheromone of the Angoumois grain moth.

It is another object of this invention to provide compounds and method of preparing same useful for the manufacture of the aforementioned sex pheromones.

How these and other objects of this invention are achieved will become apparent in the light of the accompanying disclosure. In at least one embodiment of the practices of this invention at least one of the foregoing objects will be achieved.

The isomeric components of the pink bollworm sex pheromone, i.e. (Z,Z)- and (Z,E)-7,11-hexadecadienyl acetate, are manufactured by operations involving the butylation of the mono-anion of 1,5-hexadiyne (I) to 1,5-decadiyne (II). The 1,5-decadiyne is then alkylated with hexamethylene halohydrin or a protected derivative thereof, such as the tetrahydropyranyl ether, to give the 7,11-hexadecadiynyl moiety (III) which after acetylation and partial reduction yields (Z,Z)-7,11-hexadecadienyl acetate. The Z,E isomer is prepared by the sodium liquid ammonia reduction of 1,5-decadiyne to yield deca-(E)-5-enyne which is then subsequently reacted in an analogous manner as for the production of the Z,Z isomer. The aforesaid reactions for the production of the Z,Z isomer and the Z,E isomer are indicated by the following chemical reactions:

Preparation of (Z,Z)-7,11-hexadecadienyl acetate

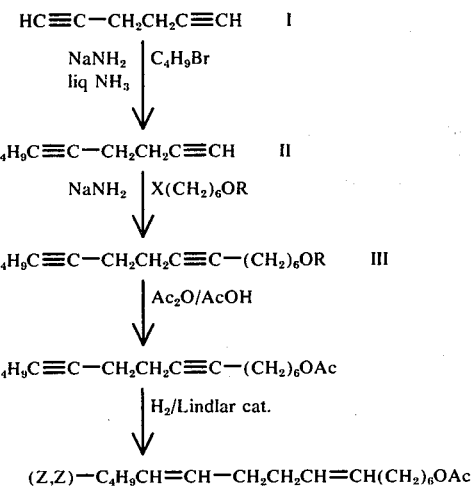

wherein R = H or 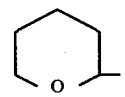

Preparation of (Z,E)-7,11-hexadecadienyl acetate

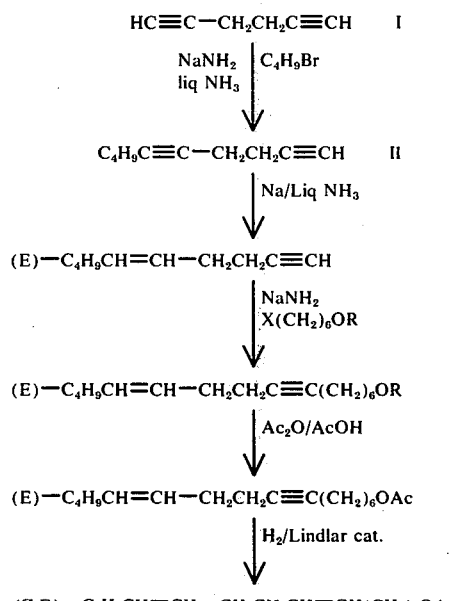

wherein R = H or 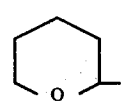

In the above-indicated reactions for the preparation of (Z,Z)- and (Z,E)-7,11-hexadecadienyl acetate, instead of sodium amide, lithium amide may be employed to generate the anions of hexadiyne decadiyne and decenyne. The solvents employed, such as tetrahydrofuran, dioxane, hexamethylphosphoramide and tetramethyl urea may be used alone or in admixture with each other or with liquid ammonia to facilitate the various reactions. Following is a more detailed description of the completion of the various steps and reactions for the preparation of (Z,Z)-7,11-hexadecadienyl acetate and (Z,E)-7,11-hexadecadienyl acetate.

Preparation of (Z,Z)-7,11-hexadecadienyl Acetate 1,5-Decadiyne

Four hundred sixty eight grams (6 mols) of 1,5-hexadiyne is added to a stirred suspension of 240 g (6.15 mols) of sodium amide in approximately 11 liters of liquid ammonia. Formation of the anion is somewhat exothermic. After ½ hour, 904 g (6.6 mols, 10% excess) of butyl bromide is added over a period of 1 hour and the resulting mixture is stirred overnight. Water (7 liters) is added cautiously to dilute the reaction mixture and give a top layer consisting of unreacted 1,5-hexadiyne, 1,5-decadiyne and 5,9-tetradecadiyne and the lower aqueous layer of inorganic salts and ammonia. The upper layers separated, washed with dilute hydrochloric acid, water and then saturated salt solution and initially distilled at 80 torr. The low boiling 1,5-hexadiyne is collected in dry-ice cooled receiver, 1,5-decadiyne, $n_D^{21}$ 1.4550, is collected at 84°–86°/30 torr and amounts to approximately 400 grams (50% based on starting 1,5-hexadiyne). 5,9-tetradecadiyne is collected at 110°–112°/2 torr and amounts to approximately 180 grams. (15% based on starting 1,5-hexadiyne). The yields of 1,5-decadiyne range between 40 and 60%.

If lithium amide is used in place of sodium amide essentially the same results are obtained. Moreover, 1,5-decadiyne can be synthesized from the lithium salt of 1,5-hexadiyne, prepared in the usual manner, and butyl bromide in dioxane-HMPA, and tetrahydrofuran-HMPA mixtures.

7,11-Hexadecadiynyl acetate

Two hundred and thirty grams of 1,5-decadiyne (1.7 mols) in 1200 ml of tetrahydrofuran is added to a suspension of 39 g (1.6 mols) of lithium amide in approximately 5 liters of liquid ammonia. After 3 hours, 224 g (0.85 mol) of the tetrahydropyranyl ether of hexamethylene bromohydrin was added to the deep red solution, and the mixture was then stirred overnight. Most of the ammonia was allowed to evaporate and water is then cautiously added to the residue. The bottom aqueous layer is extracted once with ether and combined with the upper organic layer, which is then washed once with water, followed by saturated salt solution. Ether and THF are removed on a roto vap and the residue is refluxed for 4 hours with a mixture of 500 ml glacial acetic acid and 100 ml of acetyl chloride. Then about 400 ml of acetic acid and other low boiling products are distilled off and residue is poured into ice water. The lower aqueous layer is extracted with ether, combined with the upper layer, washed, etc., and distilled, yielding 145 g (0.52 mols) 7,11-hexadecadiynyl acetate by 130°–132°/torr, $n_D^{21}$ 1.4706 (61% based on starting THP derivative of hexamethylene bromohydrin).

Instead of lithium amide, sodium or potassium amides may be used, with essentially comparable results.

The use of a protected derivative of 6-bromohexanol can be avoided thus an excess of lithium 1,5-decadiyne in liquid ammonia is used and allowed to react directly with 6-bromohexanol to give 7,11-hexadecadiynol (bp 136°–138°/1 torr, $n_D^{21}$ 1.4818). Acetylation with acetic anhydride or acetic acid-acetyl chloride converts the alcohol to the acetate.

Coupling of 1,5-decadiyne with 6-bromohexanol and/or its THP derivative can be effected in solvents other than liquid ammonia. For example, THF, dioxane, HMPA, etc.

(Z,Z)-7,11-Hexadecadienyl Acetate

Into a 500 ml Parr hydrogenation flask fitted with an aluminum or copper cooling coil is placed 100 g of 7,11-hexadecadiynyl acetate, 100 ml hexane (olefin free), 1 g palladium on calcium carbonate (Lindlar catalyst) and 10 drops of synthetic quinoline. Hydrogenation is effected at 10-20 psi and is complete when the theoretical amount of hydrogen for the partial reduction of two triple bonds is absorbed. During the hydrogenation the reaction temperature is maintained between 15°–25° to minimize cis-trans isomeration. The catalyst is then removed by filtration and the product isolated by distillation of the filtrate. bp 130°–132°/1 torr $n_D^{21}$ 1.4592. Yield essentially quantitative. Based on IR analysis it is estimated that there is less than 5% of E isomers present.

Preparation of (Z,E)-7,11-hexadecadienyl Acetate
(E)-11-Hexadecen-7-ynyl acetate To 8 liters of liquid ammonia, 230 grams of sodium (10 g-atoms) was added to give the deep blue solution of the solvated electron. THF (1 liter) is then added, followed by the addition of 1,5-decadiyne (536 g, 665 ml, 4 mols) in 1 liter of THF during 0.5 hour. The reaction is slightly exothermic and is complete after stirring an additional 0.5 hour. The blue color is sometimes discharged and replaced by the violet to purple color of the enyne anion. A sample taken for analysis was decomposed by water and found to consist of approximately 10–20% (E)-1,5-decadiene, 70–80% (E)-5-decen-1-yne and 0–5% unreacted 1,5-decadiyne (via glpc analysis, silicon grease column).

(E)-5-decen-1-yne can be isolated by the cautious addition of water to the reaction mixture and working up the product as described for 1,5-decadiyne. (E)-5-decen-1-yne is separated from the other hydrocarbon products by fractionation at 30 torr.

However, it is more convenient to use the crude hydrocarbon mixture directly in the liquid ammonia as follows:

The excess sodamide (~6.6 mols, 6.0 theoretical) is neutralized by cautiously adding 350 g ammonium chloride (6.6 mols). The resulting purple-violet solution consists of the sodium salts of 1,5-decadiyne and (E)-5-decen-1-yne. The diene does not form an anion under the conditions and its presence is compensated for by adjusting the amount of ammonium chloride added.

The THP derivative of hexamethylene bromohydrin in THF is added and the reaction mixture is worked up as described for 7,11-hexadecadienyl acetate. Vacuum distillation of the residue affords (E)-11-hexadecen-7-ynyl acetate, bp 134°–136°/1 mm, $n_D^{21}$ 1.4655, in about 55–60% yield, contaminated with 0–5% of 7,11-hexadecadiynyl acetate.

The use of a protected derivative of 6-bromohexanol can be avoided. Thus, an excess of lithium (E)-5-decen-1-yne in liquid ammonia is used and allowed to react directly with 6-bromohexanol to give (E)-11-hexadecen-7-yne-1-ol, bp 134°–136°/1 mm, $n_D^{21}$ 1.4755. Acetylation converts the alcohol to the above acetate.

Pure (E)-11-hexadecen-7-ynyl acetate can be prepared by using pure (E)-5-decen-1-yne following the procedure described for 1,5-decadiyne.

(Z,E)-7,11-Hexadecadienyl acetate is prepared by the partial reduction of (E)-11-hexadecen-7-ynyl acetate in accordance with the procedure described for (Z,Z)-7,11-hexadienyl acetate. bp 132°–134°/1 mm, $n_D^{21}$ 1.4591.

Gossyplure is prepared by mixing in equal proportions (Z,E)- and (Z,Z)-7,11-hexadecadienyl acetates which were prepared as described above.

Various compounds mentioned herein and produced and employed in accordance with the practices of this invention for the preparation of (Z,Z)- and (Z,E)-7,11-hexadecadienyl acetate are not only useful as indicated herein for the synthesis of the aforementioned compounds, particularly as intermediates, but are also useful for other purposes, such as for example, as fuel components, as gasoline and fuel oil additives and the like. Such compounds include 1,5-decadiyne and the compound $C_4H_9$—CHCH—$CH_2$—$CH_2$—C≡C$(CH_2)_6$OTHP wherein THP is tetrahydropyrane or an acyl group or other equivalent protective group.

As will be apparent to those skilled in the art in the light of the foregoing disclosure modifications, alterations and substitutions are possible in the practice of this invention without departing from the spirit or scope thereof.

We claim:

1. The compound (E)-11-hexadecen-7-ynyl acetate.

* * * * *